United States Patent
Kelman

Patent Number: 5,417,654
Date of Patent: May 23, 1995

[54] ELONGATED CURVED CAVITATION-GENERATING TIP FOR DISINTEGRATING TISSUE

[75] Inventor: Charles D. Kelman, New York, N.Y.

[73] Assignee: Alcon Laboratories, Inc., Fort Worth, Tex.

[21] Appl. No.: 190,262

[22] Filed: Feb. 2, 1994

[51] Int. Cl.⁶ .......................................... A61M 35/00
[52] U.S. Cl. ........................................ 604/22; 601/2;
604/19; 604/20; 604/21; 606/169; 606/170; 606/171; 607/115; 607/116
[58] Field of Search .................. 604/19–22; 607/111–116; 606/159, 169–171; 601/2

[56] References Cited

U.S. PATENT DOCUMENTS

| | | |
|---|---|---|
| 2,022,065 | 11/1935 | Wappler . |
| 3,012,322 | 12/1961 | Thompson . |
| 3,589,363 | 6/1971 | Banko et al. . |
| 3,645,497 | 2/1972 | Nyboer . |
| 3,794,040 | 2/1974 | Balamuth . |
| 3,857,387 | 12/1974 | Shock . |
| 3,902,495 | 9/1975 | Weiss et al. . |
| 3,958,573 | 5/1976 | Wiley . |
| 3,990,452 | 11/1976 | Murry et al. . |
| 4,136,700 | 1/1979 | Broadwin et al. . |
| 4,169,984 | 10/1979 | Parisi . |
| 4,301,802 | 11/1981 | Poler . |
| 4,465,470 | 8/1984 | Kelman . |
| 4,526,571 | 7/1985 | Wuchinich . |
| 4,535,759 | 8/1985 | Polk et al. . |
| 4,561,438 | 12/1985 | Bonnet et al. . |
| 4,570,632 | 2/1986 | Woods . |
| 4,634,419 | 1/1987 | Kreizman et al. . |
| 4,674,500 | 6/1987 | DeSatnick . |
| 4,689,040 | 8/1987 | Thompson . |
| 4,750,488 | 6/1988 | Wuchinich et al. . |
| 4,832,683 | 5/1989 | Idemoto et al. . |
| 4,869,715 | 9/1989 | Sherburne . |
| 4,869,716 | 9/1989 | Smirmaul . |
| 4,909,249 | 3/1990 | Akkas et al. . |
| 4,922,902 | 5/1990 | Wuchinich et al. . |
| 4,959,049 | 9/1990 | Smirmaul . |
| 4,974,581 | 12/1990 | Wiksell . |
| 4,989,588 | 2/1991 | Kubota et al. . |
| 5,084,012 | 1/1992 | Kelman . |
| 5,112,339 | 5/1992 | Zelman . |
| 5,154,694 | 10/1992 | Kelman . |
| 5,163,433 | 11/1992 | Kagawa et al. . |
| 5,213,569 | 5/1993 | Davis . |
| 5,222,937 | 6/1993 | Kagawa . |
| 5,242,449 | 9/1993 | Zaleski . |
| 5,255,669 | 10/1993 | Kubota et al. . |

FOREIGN PATENT DOCUMENTS

| | | |
|---|---|---|
| 0238667 | 9/1987 | European Pat. Off. . |
| 0456470 | 11/1991 | European Pat. Off. . |
| 06515 | 7/1989 | WIPO . |
| 10139 | 6/1992 | WIPO . |

OTHER PUBLICATIONS

Steriseal "Retractors Iris Retraction Cannulae", 1 page.
Stoiz® CANNUALS, p. 17.
RHEIN Medical, "Universal I/A Handpiece With Interchangeable Tip", 1 page.

*Primary Examiner*—C. Fred Rosenbaum
*Assistant Examiner*—Bryan L. Tsosie
*Attorney, Agent, or Firm*—Darby & Darby

[57] ABSTRACT

An improved tip for use with a device for disintegrating tissue located in a predominantly liquid environment. The tip is connected to an oscillation generator, which results in ultrasonic oscillating movement along the tip axis. When placed within the posterior capsule of an eye, the tip causes the tissue of the natural lens in close proximity to disintegrate. The tip has an elongated curved portion having a convex front surface, a concave rear surface and a rear-facing end surface. The elongated curve of the tip and the rear facing end surface allow easy access to all areas of the capsular bag, some of which were relatively unreachable with known ultrasonic tips.

14 Claims, 2 Drawing Sheets

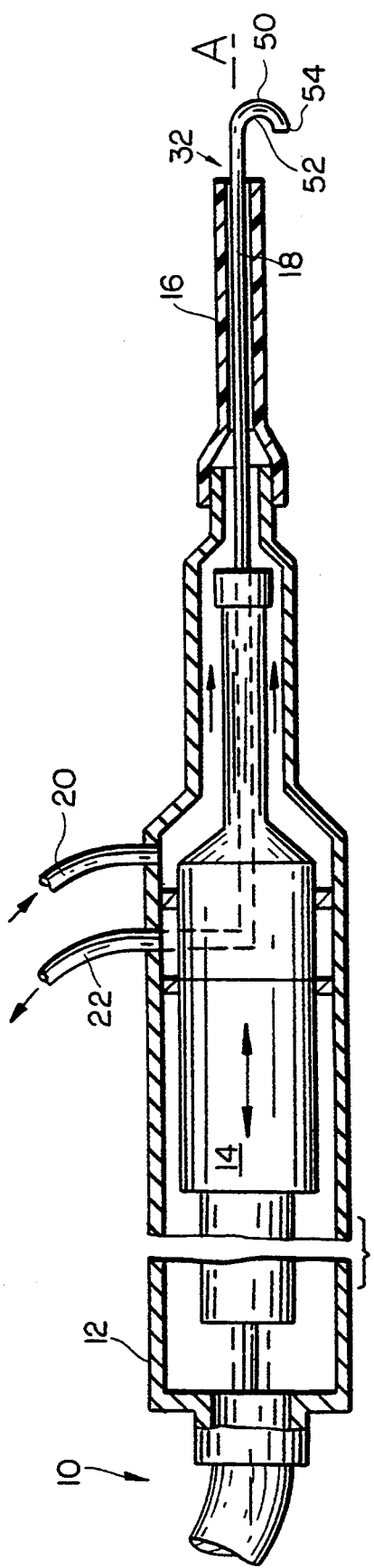
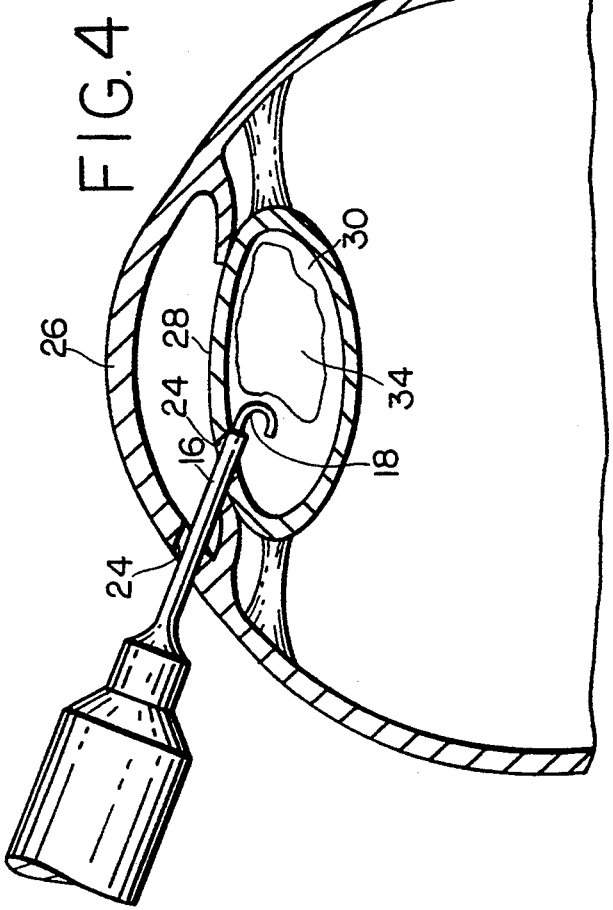
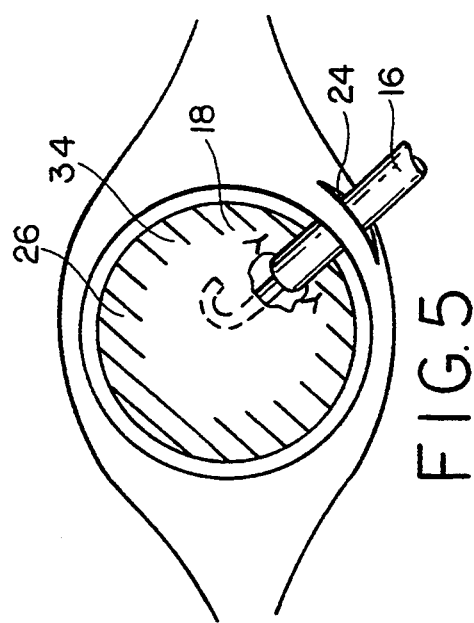

ELONGATED CURVED
CAVITATION-GENERATING TIP FOR
DISINTEGRATING TISSUE

FIELD OF THE INVENTION

The present invention relates to a device for use in the medical field for assisting in the disintegration and removal of tissue, and more particularly to an improved tip element of such a device which is specifically designed for extracting the cataracted natural lens from the eye of either a human or an animal.

BACKGROUND OF THE INVENTION

A now common medical procedure in eye surgery involves the complete removal of a cataracted lens from a human eye to be later replaced with an intraocular artificial lens. The known procedure includes making an incision in the cornea. To minimize patient trauma and unnecessary tissue damage, this incision is kept very small. The entire operation of disintegrating and removing the damaged natural lens tissue is performed using instruments placed through the small incision. A small vibratory instrument is used to assist in the lens tissue disintegration. The cutting tip is generally tubular and is oscillated by the instrument along its axis at a very high frequency. The cutting tip is inserted into the incision and maneuvered by the surgeon throughout accessible portions of the capsular bag containing the natural lens. The movement of the vibrating cutting tip causes the lens tissue to disintegrate. As the lens breaks apart, the resulting loose lens particles are aspirated from the capsular bag under vacuum by way a first conduit in the tubular cutting tip of the vibrating instrument.

U.S. Pat. No. 3,589,363 to Banko and Kelman discloses such a hand held instrument for breaking apart and removing tissue from a body site, such as cataracted lens tissue from a human eye. The content of U.S. Pat. No. 3,589,363 hereby incorporated by reference.

There are several problems encountered by surgeons using the above procedure. A first problem is that in addition to the incision in the cornea a substantial portion of the anterior wall of the capsular bag must be removed, in order for the straight end of the tip to have at least some maneuverability in the capsular bag, since an intermediate portion of the tip is essentially fixed in space by its extending through the small corneal incision spaced from the capsular bag. Even after such removal, however, of the anterior capsular wall the geometry of the eye and the location of the incision restrict the accessibility of the surgeon's operating instruments within the capsular bag. In other words, the typically straight cutting tips of the vibratory instrument cannot easily be maneuvered within the capsular bag to effectively reach all parts of the lens to be removed. The straight tips may be angled slightly from side to side, but cannot be angled sufficiently to allow the working end of the tip to reach the areas at the peripheral interior regions of the capsular bag, at least not without removal of a substantial portion of the anterior capsular wall.

To overcome this accessibility problem with the known cutting tips, cutting tips have been made with varying bends, up to 90 arc-degree bends, so that the cutting tip may be maneuvered to reach additional parts of the posterior cavity while operating through the pair of spaced incisions. This bent cutting tip feature is disclosed in my U.S. Pat. No. 5,154,694, the content of which is incorporated herein by reference. Other improvements to cutting tips with less than 90 arc-degree bends are shown in my co-pending applications, Ser. No. 07/958,651, filed Oct. 8, 1992, entitled CAVITATION-GENERATING TIP FOR DISINTEGRATING TISSUE, and Ser. No. 08/055,213, filed Apr. 28, 1993, entitled BENT PHACO-TIP WITH SAFETY EDGES.

Even with these bent tips, however, the regions at the outermost peripheral portion at the interior of the capsular bag are not readily accessible to the tip without substantial opening of the anterior capsular wall. Where it is desired to minimize the opening in the anterior capsular wall, a further improved cutting tip is required.

It has been determined by the applicant that the disintegration of tissue in the immediate vicinity of the cutting tip is enhanced by the cavitation effect resulting from the ultrasonic oscillation of the cutting tip within the liquid filled environment of the capsular bag, i.e., posterior capsule.

Whenever any object having a distinct frontal surface area, with respect to the direction of movement, moves relatively quickly within a fluid, a low pressure region (i.e., negative pressure relative to the surrounding fluid) is developed just behind, or adjacent to, such frontal surface. If the magnitude of the negative pressure developed within the low pressure region becomes greater than the negative pressure required to vaporize the particular fluid, the fluid will be vaporized, creating bubbles called cavitation bubbles.

Thus, when the cutting tip of the above-described vibratory instrument moves in a direction away from the surface of the tissue to be disintegrated, a sudden low pressure region is developed within the adjacent fluid resulting in the formation of cavitation bubbles, It is believed that during each ultrasonic oscillation, as the cutting tip continues to move away from the tissue surface, the pressure in the expanding newly formed cavitation bubbles decreases. It is further believed that when the point is reached, during the cycle, where the fluid pressure outside the bubble exceeds the pressure in the expanding cavitation bubbles, there results a collapse of the cavitation bubbles and they are quickly re-absorbed into the fluid. The pressure waves in the fluid resulting from the substantially simultaneous collapsing of thousands of such tiny bubbles, operate on the nearby tissue to help disintegrate it. The rate of "collapse" of the cavitation bubbles determines the degree of assistance to disintegrating the nearby tissue. The greater the number of cavitation bubbles formed and the quicker the rate of collapse of the bubbles, the greater will be the desired damage to the nearby tissue.

It is an object of the invention to provide a cutting tip for use with a vibratory instrument which will provide even greater accessibility to previously inaccessible tissue and to provide at least one additional surface to produce the cavitation bubbles.

It is another object of the invention to provide a cutting tip that causes the disintegrated material to be drawn to the tip end, thus exposing the remaining tissue ultrasonic disintegration.

It is a further object of the invention to provide a cutting tip which will provide the maximum cavitation bubbles to more effectively disintegrate the tissue.

It is a concomitant object of the invention to provide a cutting tip which is so shaped that forwardly and rearwardly facing portions will generate cavitation bubbles for softening or for disintegration of tissue lying forwardly and rearwardly of the tip while the tip end also generates cavitation bubbles for disintegrating tissue lying rearwardly of the tip.

SUMMARY OF THE INVENTION

An improved tip for use with a device for disintegrating tissue located in a predominantly liquid environment. The device includes an oscillation generator which provides ultrasonic reciprocating movement along the axis of the device. When placed within the posterior cavity, the tip causes the tissue in close proximity to disintegrate. The tip has an elongated curve that forms a curved frontal surface, a rear surface and a rear-facing end surface. All three of these surfaces create cavitation bubbles within the liquid during the reciprocating strokes of the entire tip. Since the tip is curved, the curve is elongated and the end surface faces rearwardly, it provides easy access to all areas of the posterior capsule, some of which were relatively unreachable with known ultrasonic tips. The tip may also include a vacuum inlet opening at its rear-facing surface. Since the opening is away from the front surface, disintegrated tissue is drawn away from the front surface.

BRIEF DESCRIPTION OF THE DRAWINGS

The foregoing and other objects and advantages will become apparent to those skilled in the art upon reading the following detailed description of the preferred embodiments, in conjunction with a review of the appended drawings, in which:

FIG. 3 is an overall cross-sectional side view of a vibratory instrument showing a tip in accordance with the present invention attached thereto;

FIG. 4 is a partial cross-sectional side view of an eye showing the vibratory instrument including the cutting tip in an operational position in accordance with the invention;

FIG. 5 is a front view of the eye of FIG. 4;

DETAILED DESCRIPTION OF THE PREFERRED EMBODIMENTS

Figure 1:
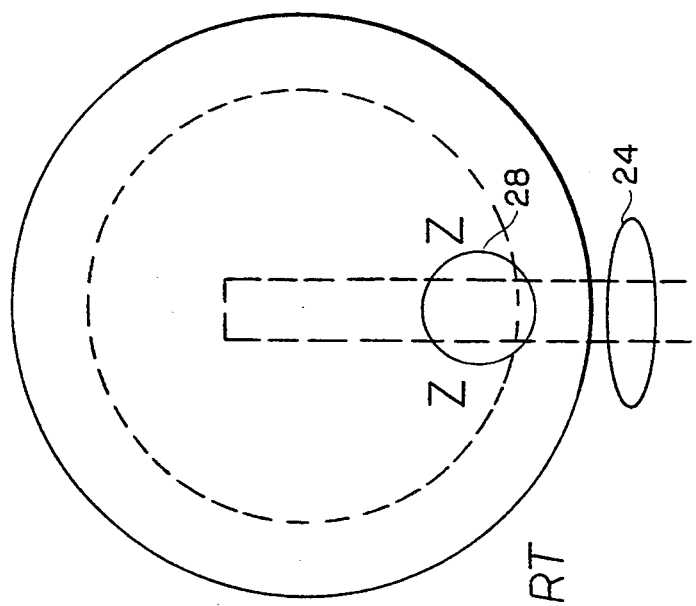
FIG. 1 is a front schematic view of an eye under treatment with an oscillating straight tip according to the prior art, but with only a small incision made in the anterior wall of the posterior capsule.

Referring to prior art FIG. 1, a vibratory instrument according to the prior art is shown. The instrument is inserted through small incisions in the cornea and in the anterior wall of the posterior capsule containing the cataracted natural lens. As seen in FIG. 1, while being able to angle the instrument to some degree, it is impossible to have the working end of the straight tip (where the disintegration takes place) come into proximity with any cataracted material that is to the immediate sides of the capsular incision (areas Z, FIG. 1) except by making the incision 28 nearly as large as the entire capsular bag.

Other known tips include bends that provide slightly more access than the tip shown in FIG. 1. For example, there are tips that include an approximately 20° bend with an end surface perpendicular to the axis of the instrument. This can increase the surface area of the end surface, but only minimally increases the access afforded by the tip. For example, areas Z in FIG. 1 would still be inaccessible. Known tips with a 90° bend afford much greater access to the cataracted material, but are still unable to easily reach material that is located behind and to the side of the incision in the bag (see, for example, areas Y in FIG. 5).

Thus, referring to FIGS. 2–6, a vibratory instrument 10 is shown having a curved elongated tip 18. The instrument includes a housing 12, an internal ultrasonic oscillation generator 14, a sleeve 16 and a tubular cutting tip 18. The protective sleeve 16 is tubular and is attached to the housing 12. The protective sleeve 16 is stationary with respect to the housing 12 and, once inserted in the eye, is also stationary with respect to the eye. The cutting tip 18 is positioned within the tubular protective sleeve 16 and is attached to a forward end of the oscillation generator 14. The oscillation generator 14 reciprocates the cutting tip 18 along an axis A at a predetermined ultrasonic oscillation rate. The instrument 10 also preferably includes an irrigation fluid inlet line 20 which is in fluid communication with the tubular protective sleeve 16 and an aspirating fluid outlet line 22 which communicates in a well known manner with an internal passage in the tubular cutting tip.

Figure 2:
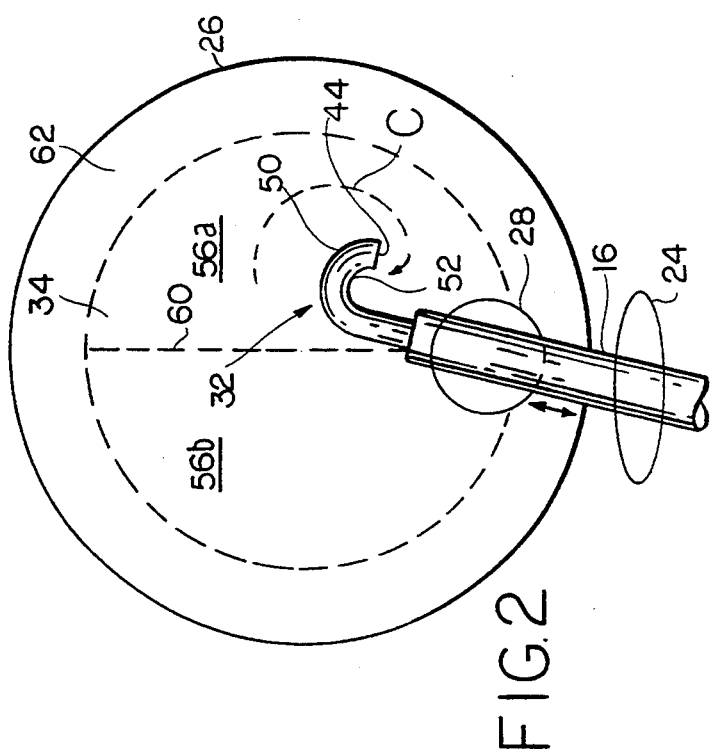
FIG. 2 is a front schematic view of an eye under treatment with an oscillating tip according to the present invention.

As described above, a small incision 24 is made in the cornea 26 and an opening 28 is made in the anterior wall of the capsular bag 30 using a scalpel or similar cutting instrument. Together, these two openings provide access to the interior of the capsular bag 30 through which the cutting tip of the vibratory instrument 10 is inserted by a surgeon, as shown in FIGS. 2, 4 and 5. The protective sleeve 16 contacts the tissue of the cornea 26 adjacent the small incision 24. The purpose of the protective sleeve 16 is to protect the healthy tissue (i.e., the tissue lying adjacent the incision 24) from the oscillating cutting tip 18 positioned therein. The protective sleeve 16 also provides one-way isolated fluid communication directly with the posterior capsule 30 for providing irrigation fluid to the surgical site.

The cutting tip 18 is also positioned through incision 24 but operates within the protective sleeve 16. A forwardmost portion 32 of the cutting tip 18 extends past the protective sleeve 16 and into contact with the cataracted natural lens 34. As the generator 14 oscillates the cutting tip 18 back and forth along axis A, the surfaces of the tip 18 that are transverse to the axis will cause cavitation bubbles to be formed in the regions extending from those surfaces. The bend of the tip forms a front surface 50 and a rear surface 52, both of which will form cavitation bubbles to disintegrate the cataracted tissue. The front edge (i.e., rearwardly facing surface) 54 of the tip end will also form cavitation bubbles to disintegrate the cataracted tissue facing it. The exact curvature of the tip bend is not critical, although curves having a larger or smaller radius will affect the size of the cavitation-forming surfaces, and so will affect the effectiveness of the tip. The bend of the tip is preferably 180 degrees, although any bend between approximately 160 degrees and 180 degrees is sufficient.

As seen in FIG. 2, the front surface 50 will tend to soften or disintegrate material ahead of the tip 18 along the axis A. Preferably, the area affected by the front surface 50 will act on half of the lens material 56a in the capsular bag 30 at a time. The rear surface 52 will tend to disintegrate material immediately adjacent the sleeve 16 and the tip 18. Once the first half of the lens material 56a in the capsular bag 30 is disintegrated and aspirated (described more fully below), the tip may be rotated 90 degrees along axis A to disintegrate the other half of the lens material 56b in the bag 30.

The rate of oscillation of the generator 14 is preferably in the range between 10 kHz and 60 kHz, more preferably between 40 kHz and 60 kHz. The exact frequency used depends on several factors, including the precise shape of the tip 18, the type of tissue being disintegrated and the degree of disintegration desired. The tip is preferably formed of a titanium alloy, although any medically inert material capable of withstanding the ultrasonic oscillations without melting, fragmenting or otherwise being damaged may be used similarly.

Figure 6:
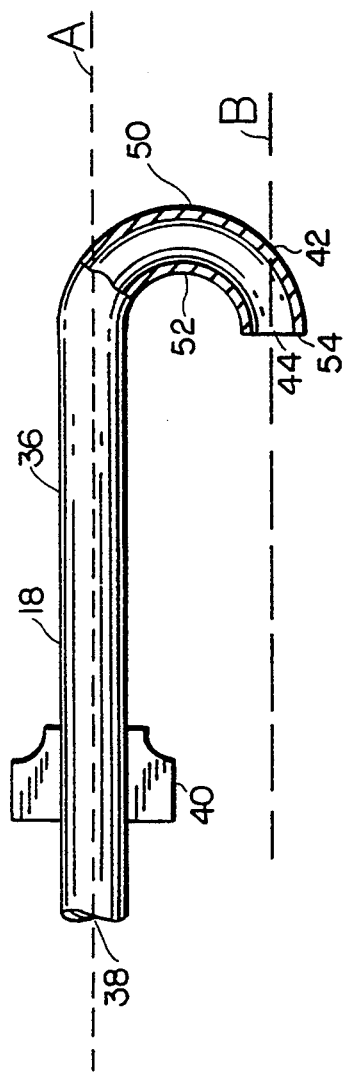
FIG. 6 is a partial, sectional side view of a cutting tip assembly in accordance with a preferred embodiment of the invention.

Referring to FIG. 6, a cutting tip 18 in accordance with the invention is shown having a tip shaft or tube 36 positioned along an axis A, a connection end 38, a securing flange 40 and a tip end 42. The tip end 42 includes a tip opening 44 and the front edge 54. As the cutting tip 18 oscillates along the longitudinal axis A, the opening 44 moves along an axis B that is parallel to but displaced from axis A.

To break up the cataracted lens, the surgeon first inserts the tip 18 into the capsular bag 30 by placing the tip end against the incision 28 and then twisting the tip 18 into the bag 30 as though threading a hook into the incision. Once inserted, the surgeon uses the vibrating cutting tip 18 to make a shallow groove 60 generally along the axis of the oscillation and near the center of the lens 34. The surgeon then elongates and deepens the groove until it extends across the lens 34 and almost completely therethrough. The groove 60 is made deeper by removing small amounts of cataracted tissue along the groove 60 until the lens 34 cracks into two more manageable half sections 56a,56b.

In carving out the groove 60, the lens 34 has now become somewhat smaller in volume. However, the complete removal of the lens now requires that each of the two half sections 56a,56b be disintegrated. To disintegrate a half section in a controlled manner, the surgeon positions the cutting tip 18 against the section. The surgeon uses the cavitation effects at the front surface 50, rear surface 52 and rear-facing front edge 54 of the oscillating tip 18, together with the suction of the aspiration fluid moving through the tube 36 to effectively and quickly disintegrate the half section.

As the front surface 50 moves away from the tissue of the half section 56a during one half of each reciprocation cycle, a negative pressure is generated in the fluid between the front surface 50 and the tissue surface. This negative pressure causes cavitation bubbles to form both on and adjacent the surface of the tissue and within the cells making up the tissue. As the pressure increases, the cavitation bubbles collapse as they are absorbed back into the surrounding fluid. It is believed that this collapse of cavitation bubbles causes cell walls to burst apart to thereby disintegrate the tissue. The same effect occurs at the rear surface 52 acting on lens material adjacent that surface and at the front edge 54 on material ahead of the tip end. Thus, significant disintegration occurs at the tip end 42 as well as at the surfaces 50, 52.

As the cavitation-assisted disintegration of tissue of the half section 56a continues, the vacuum from the aspiration of fluid continuously pulls the small particles of natural lens tissue around to the tip end 42 in a rotation-like motion (see arrow C, FIG. 2). This has the effect of drawing fragmented portions of the lens that are farther away from the front surface 50 of the tip 18 toward the front surface 50 and the front edge 54 to be more effectively disintegrated at those surfaces. As the surgeon moves the tip 18 around the half section 56a of the lens, all of the disintegrated material is eventually removed. The surgeon can then rotate and angle the tip 18 to disintegrate the opposite half 56b of the cataracted natural lens in the same manner.

In the above-described preferred embodiment of the invention, the outside diameter of the tip is preferably in the range of 0.5 mm to 0.9 mm and the wall thickness is about 0.05 mm to 0.15 mm. The diameter of the opening 44 is preferably 0.4 mm to 0.8 mm. The elongated curved portion of the tip is approximately 1 mm to 1.8 mm wide, i.e. the distance between parallel axes A and B (FIG. 6).

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. A device for disintegrating tissue located in a predominantly liquid environment, said device including an oscillation generator providing an oscillation movement along a first axis at an ultrasonic frequency, a cutting tip having a proximal end and a distal end and operatively connected to said oscillation generator to be drawn and advanced in oscillating movement along said first axis, said cutting tip being positioned in proximity to said tissue wherein said oscillation of said cutting tip causes said tissue to disintegrate, said cutting tip being tubular and having a curved section intermediate said distal end and said proximal end, and terminating at said distal end in an exposed opening said opening facing in the general direction of said proximal end of said cutting tip and having a peripheral edge around said opening, said opening lying in a plane generally transverse to said first axis, said edge defining a surface generally transverse to said first axis of movement.

2. A device for disintegrating tissue according to claim 1, wherein said plane is substantially perpendicular to said first axis.

3. A device for disintegrating tissue according to claim 1, wherein said distal end oscillates along a second axis of movement, said second axis of movement being substantially parallel to and offset from said first axis.

4. A device for disintegrating tissue according to claim 1, wherein said curved section defines a convex region facing in a direction away from said proximal end and a oppositely facing concave region.

5. A device for disintegrating tissue according to claim 1, wherein said tube is hollow such that fluid may pass between said proximal end and said distal end.

6. A device for disintegrating tissue according to claim 4, wherein said convex and said concave regions are alternately create and subsequently collapse cavitation bubbles thereby assisting in the disintegration of the adjacent tissue.

7. A device for disintegrating tissue according to claim 4, further comprising a source of vacuum connected to said tube for causing fluid and disintegrated tissue to be drawn into said tip such that tissue adjacent said convex region will be drawn away from said convex region toward said opening once said tissue is disintegrated.

8. A device for disintegrating tissue according to claim 1, wherein said curved section is bent between 160 and 180 arc-degrees.

9. A device for disintegrating tissue according to claim 1, wherein said tip has a medial portion between said distal and said proximal ends, further comprising:

a sleeve surrounding at least said medial portion of said tip, said curved section and said distal end extending beyond said sleeve.

10. A device for disintegrating tissue according to claim 1, wherein said surface is shaped and constructed to form cavitation bubbles for disintegrating tissue in the region of said opening.

11. A device for disintegrating tissue according to claim 10, wherein said rearwardly opening extends rearwardly along a second axis spaced from said first axis.

12. A device for disintegrating tissue according to claim 11, wherein said first and second axes are substantially parallel.

13. A device for disintegrating tissue according to claim 12, wherein said first and second axes are spaced between approximately 1 mm to 1.8 mm apart.

14. A device for disintegrating tissue, said device including a handle and a cutting tip having a proximal end and a distal end and operatively connected to said handle, said cutting tip comprising:

a tube having a curved section near said distal end, said curve covering between 160 and 180 arc-degrees such that said distal end terminates in a surface lying in a plane generally transverse to said first axis.

* * * * *